(12) United States Patent
Baker, Jr.

(10) Patent No.: US 8,704,666 B2
(45) Date of Patent: Apr. 22, 2014

(54) MEDICAL DEVICE INTERFACE CUSTOMIZATION SYSTEMS AND METHODS

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 1193 days.

(21) Appl. No.: 12/563,841

(22) Filed: Sep. 21, 2009

(65) Prior Publication Data

US 2011/0071368 A1 Mar. 24, 2011

(51) Int. Cl.
 *G08B 23/00* (2006.01)
(52) U.S. Cl.
 USPC .................................................. 340/573.1
(58) Field of Classification Search
 None
 See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,941,174 A * | 7/1990 | Ingham ........................... 380/52 | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,303,291 A * | 4/1994 | Takagi et al. ............ 379/433.13 | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |

(Continued)

FOREIGN PATENT DOCUMENTS

JP 25168600 6/2005

OTHER PUBLICATIONS

Plastic Logic;http://www.plasticlogic.com/product.html; 2000.

(Continued)

*Primary Examiner* — Brian Zimmerman
*Assistant Examiner* — Kevin Lau (57) ABSTRACT

Embodiments of the present disclosure relate to customization of user interfaces for medical devices. According to certain embodiments, patient monitors may include a device body designed to interface with interchangeable and removable faceplates. The faceplates may include input devices for controlling the patient monitor. Further, the properties of the input devices, such as the size, shape, labels, type, and location, may vary between faceplates. Further, in certain embodiments, the faceplates may include a memory for storing preferences associated with the user interface.

20 Claims, 7 Drawing Sheets

(56) References Cited

U.S. PATENT DOCUMENTS

| | | |
|---|---|---|
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Kuenstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,848,152 A * | 12/1998 | Slipy et al. ............... 379/433.13 |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,188,470 B1 | 2/2001 | Grace |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,398,727 B1 | 6/2002 | Bui et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,792,396 B2 | 9/2004 | Inda et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,095,986 B2 * | 8/2006 | Mager .......................... 455/90.3 |
| 7,127,278 B2 | 10/2006 | Melker et al. |
| 7,162,306 B2 | 1/2007 | Caby et al. |
| 7,186,966 B2 | 3/2007 | Al-Ali |
| 7,209,775 B2 | 4/2007 | Bae et al. |
| 7,236,811 B2 | 6/2007 | Schmitt |
| 7,263,395 B2 | 8/2007 | Chan et al. |
| 7,269,449 B2 * | 9/2007 | Salminen et al. .......... 455/575.1 |
| 7,272,426 B2 | 9/2007 | Schmid |
| 7,315,260 B1 * | 1/2008 | Lam et al. ....................... 341/22 |
| 7,373,193 B2 | 5/2008 | Al-Ali et al. |
| 2001/0001319 A1 * | 5/2001 | Beckert et al. ................... 701/36 |
| 2001/0005773 A1 | 6/2001 | Larsen et al. |
| 2001/0017484 A1 * | 8/2001 | Endo ............................ 307/10.1 |
| 2001/0020122 A1 | 9/2001 | Steuer et al. |
| 2001/0021799 A1 * | 9/2001 | Ohlsson ......................... 600/300 |
| 2001/0026265 A1 * | 10/2001 | Kikuchi et al. ................ 345/157 |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0030103 A1 * | 3/2002 | Wycherley et al. ........... 235/439 |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0114133 A1 * | 6/2003 | Enners .......................... 455/344 |
| 2003/0119543 A1 * | 6/2003 | Kfoury et al. ................. 455/550 |
| 2003/0139687 A1 | 7/2003 | Abreu |
| 2003/0144584 A1 | 7/2003 | Mendelson |
| 2003/0208314 A1 * | 11/2003 | Funk et al. .................... 701/207 |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |

(56) References Cited

U.S. PATENT DOCUMENTS

| | | |
|---|---|---|
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2004/0259587 A1* | 12/2004 | Chadha ............... 455/550.1 |
| 2005/0026661 A1* | 2/2005 | Rheenen et al. ......... 455/575.8 |
| 2005/0075686 A1* | 4/2005 | Phillips et al. ............. 607/60 |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2005/0286213 A1* | 12/2005 | Rooney ................. 361/679 |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0030764 A1 | 2/2006 | Porges et al. |
| 2006/0036136 A1 | 2/2006 | Shaw |
| 2006/0052680 A1 | 3/2006 | Diab |
| 2006/0058683 A1 | 3/2006 | Chance |
| 2006/0064024 A1 | 3/2006 | Schnall |
| 2006/0068834 A1* | 3/2006 | Jones ................... 455/550.1 |
| 2006/0069319 A1 | 3/2006 | Elhag et al. |
| 2006/0088335 A1* | 4/2006 | Choi .................. 399/110 |
| 2006/0114236 A1* | 6/2006 | Ray ................... 345/172 |
| 2006/0146029 A1* | 7/2006 | Diercks ................ 345/169 |
| 2006/0189871 A1 | 8/2006 | Al-Ali et al. |
| 2006/0195028 A1 | 8/2006 | Hannula et al. |
| 2006/0220881 A1 | 10/2006 | Al-Ali et al. |
| 2006/0224058 A1 | 10/2006 | Mannheimer |
| 2006/0226992 A1* | 10/2006 | Al-Ali et al. ............... 340/573.1 |
| 2006/0238358 A1 | 10/2006 | Al-Ali et al. |
| 2006/0247501 A1 | 11/2006 | Ali |
| 2006/0253010 A1 | 11/2006 | Brady et al. |
| 2006/0256090 A1* | 11/2006 | Huppi .................. 345/173 |
| 2006/0258921 A1 | 11/2006 | Addison et al. |
| 2007/0100218 A1 | 5/2007 | Sweitzer et al. |
| 2007/0100219 A1 | 5/2007 | Sweitzer et al. |
| 2007/0167693 A1 | 7/2007 | Scholler et al. |
| 2007/0188495 A1 | 8/2007 | Kiani |
| 2007/0216655 A1* | 9/2007 | Chen et al. ............ 345/173 |
| 2008/0030468 A1 | 2/2008 | Ali et al. |
| 2008/0097177 A1 | 4/2008 | Music et al. |
| 2008/0103375 A1 | 5/2008 | Kiani |
| 2008/0108884 A1 | 5/2008 | Kiani |
| 2008/0120559 A1* | 5/2008 | Yee .................. 715/764 |
| 2008/0177160 A1 | 7/2008 | Al Ali et al. |
| 2008/0183057 A1 | 7/2008 | Taube |
| 2008/0221418 A1 | 9/2008 | Al-Ali et al. |
| 2008/0242959 A1 | 10/2008 | Xu et al. |
| 2009/0025432 A1 | 1/2009 | Kim et al. .............. 68/12.27 |

OTHER PUBLICATIONS

First-Generation Electronic Paper Display from Phlips, Sony and E Ink to be Used in New Electronic Reading Devices; E Ink Corporation; 2005.
Electronic Paper Displays; E Ink Corporation; 2005.
Segmented ePaper Displays; Innovating Display Solutions; SiPix;.
Active Matrix ePaper Displays; Innovating Display Solutions; SiPix.

* cited by examiner

MEDICAL DEVICE INTERFACE CUSTOMIZATION SYSTEMS AND METHODS

BACKGROUND

The present disclosure relates generally to medical device user interfaces, and, more particularly, to customizable medical device user interfaces.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Patient monitors include medical devices that facilitate measurement and observation of patient physiological data. For example, pulse oximeters are a type of patient monitor. A typical patient monitor cooperates with a sensor to detect and display a patient's vital signs (e.g., temperature, pulse rate, respiratory rate) and/or other physiological measurements (e.g., water content of tissue, blood oxygen level) for observation by a user (e.g., clinician). For example, pulse oximeters are generally utilized with related sensors to detect and monitor a patient's functional oxygen saturation of arterial hemoglobin (i.e., $SpO_2$) and pulse rate. Other types of patient monitors, such as blood pressure monitors, may be utilized to detect and monitor other physiological parameters. Further, the patient monitors may be incorporated into other types of medical devices, such as mechanical ventilators and anesthesia machines, among others.

A patient monitor may include a screen that displays information relating to operation and use of the patient monitor. A typical patient monitor screen may display operational data that is instructive and that facilitates operation of the monitor by a user. For example, the operational data may include status indicators and instructional data relating to the monitor itself and/or monitor applications (e.g., a power indicator, an alarm silenced icon, and a battery low indicator). The screen may also display measurement data from a patient being monitored. For example, the measurement data may include information relating to a physiological feature of the patient being monitored. Specifically, the screen may display a graph or trend (e.g., a pulse rate trend, and/or a plethysmographic waveform) of data relating to particular measured physiological parameters.

A patient caretaker may navigate through various screens of a patient monitor using input devices, such as buttons, to view operational data and/or to change operating parameters, such as alarm limits, of the patient monitor. Further, the input devices may be used to customize operational aspects of the patient monitor, such as alarm volume, alarm duration, or display scales. Individual patient caretakers may desire different types of user interfaces and/or may prefer different operating parameters. However, patient monitors may be shared by several patient caretakers, which may limit customization.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to customization of user interfaces for medical devices, such as patient monitors. According to certain embodiments, the patient monitors may include a device body designed to interface with interchangeable and removable faceplates. The faceplates may include input devices for controlling the patient monitor. Further, the properties of the input devices, such as the size, shape, labels, type, and location, may vary between faceplates. For example, certain faceplates may include arrow buttons for selecting between menu options and operating parameters while other faceplates include knobs for performing these functions. Accordingly, a caretaker may customize the user interface of a patient monitor by selecting and attaching a faceplate that has the desired input device configuration.

Further, instead of or in addition to, including input devices, the faceplates may include a memory for storing preferences associated with the user interface. For example, the memory may store user interface preferences for the patient monitor, such as alarm limits, the alarm volume, the default trend view, the display layout, the preferred language, and the default display scale, among others. Upon connection of a faceplate to the device body, the patient monitor may apply the user interface preferences stored in the faceplate. Accordingly, a caretaker may customize user interface settings for the patient monitor by attaching a faceplate with the desired preferences stored within a memory of the faceplate.

Figure 1:
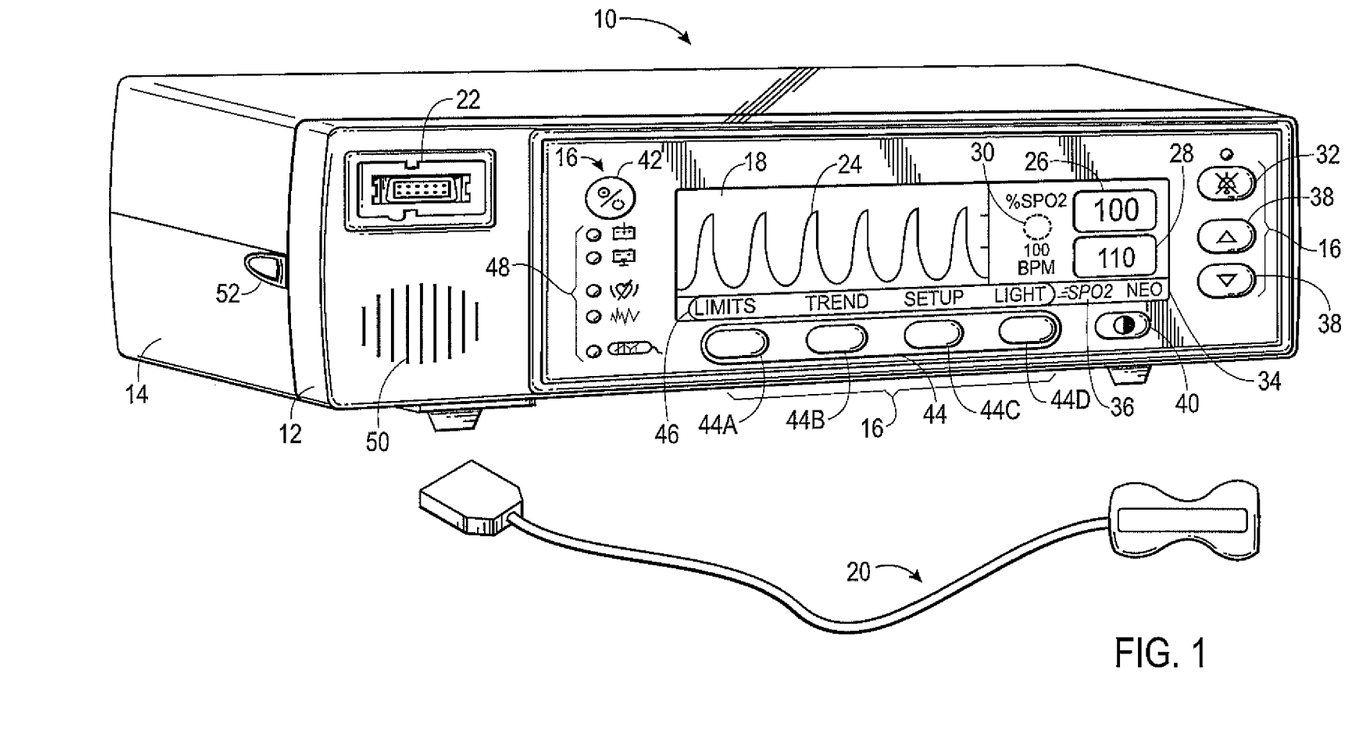
FIG. 1 is a perspective view of an embodiment of a patient monitor with an interchangeable faceplate.

FIG. 1 is a perspective view of an embodiment of a patient monitor 10. For example, the patient monitor 10 may be a pulse oximeter, such as those available from Nellcor Puritan Bennett LLC of Boulder, Colo. As shown, the patient monitor 10 is a pulse oximeter designed to detect and monitor blood oxygen saturation levels, pulse rate, and so forth. However, in other embodiments, the configurable user interfaces may be employed in other types of patient monitors, such as vital signs monitors, critical care monitors, obstetrical care monitors, or blood pressure monitors, among others. Further, the patient monitor 10 may be part of a therapeutic medical device, such as a mechanical ventilator, or anesthesia machine, among others.

The patient monitor 10 may include a removable and interchangeable faceplate 12 that may be coupled to a body 14 of the patient monitor 10. The faceplate 12 may include several selectable inputs 16 that may be actuated by a caretaker to operate the patient monitor 10. For example, the selectable inputs 16 may include buttons that may be pressed to change information shown on a display 18. In certain embodiments, the display 18 may include a cathode ray tube or liquid crystal display. Moreover, the display 18 may include an optional touch screen. In general, the display 18 may show processed physiological data and/or other data received through a medical device interface, such as a cable connection port 22, from a patient sensor 20, or other suitable medical device, such as a therapy device. As shown, the medical device interface 22 includes a cable connection port. However, in other embodiments, the medical device interface 22 may any suitable type of interface for connecting to a medical device. For example, in certain embodiments, the medical device interface 22 may include a wireless interface.

For example, the display 18 may be used to display a plethysmographic ("pleth") waveform 24, an oxygen saturation 26, and/or a pulse rate 28. The oxygen saturation 26 may be a functional arterial hemoglobin oxygen saturation measurement displayed as units of percentage $SpO_2$. The pulse rate 28 may indicate a patient's pulse rate in beats per minute. The display 18 also may be used to show topic-specific screens related to the physiological data, such as a "blip" display that includes pulse amplitude blips, a real-time trend display, and an alarm limit and monitoring mode display. Moreover, the display 18 may be used to display user interface options, such as a setup and/or configuration screen for adjusting parameters such as alarm volume, display scales, and button sizes and locations, among others.

In addition to displaying physiological information, the patient monitor 10 may also display information related to alarms and monitor settings on the display 18. For example, in some embodiments, the patient monitor 10 may employ SatSeconds™ by Nellcor™ to detect alarms and manage nuisance alarms. SatSeconds™ may include activation of an alarm based on limits that may include the integral of time and depth of a desaturation event and may include an indicator 30 that may serve to inform the caretaker that an $SpO_2$ reading has been detected outside of the limit settings. The display may also include an alarm status indicator (not shown), such as a bell that flashes when an alarm condition is present. One of the input devices, such as an alarm silence button 32, may be actuated to silence the alarm and display an alarm silence indicator (not shown), such as a slash and a timer, on the display 18. The display 18 also may show mode setting information describing a specific mode to which the alarm limits are set. For example, the display 18 may show an indicator 34 that informs a caretaker that neonatal alarm limits are currently applied rather than adult alarm limits. In another example, the display 18 may show an indicator 36 that informs a caretaker that the patient monitor 10 is operating in a fast alarm response mode rather than a normal alarm mode.

In general, the selectable inputs 16 may be used to control operating functions of the patient monitor 10. The selectable inputs 16 may include fixed function keys, such as the alarm silence button 32, arrow keys 38, a contrast selection key 40, and a power key 42. For example, the arrow keys 38 may be actuated to adjust alarm limits and/or to vary the physiological information shown on the display 18. In another example, the contrast selection key 40 may be actuated to adjust the contrast of the display 18. Further, the fixed function keys may be programmed to control multiple functions or to operate in different manners based upon various factors, such as the duration the key is pressed, the simultaneous activation of other keys, and so forth. For example, an arrow key 38 may be configured to scroll upwards or downwards more rapidly based upon how long the respective key is held down.

The monitor 10 also may include programmable function keys ("soft keys") 44, and associated soft key icons in the soft key menu 46. Each of the four soft keys 44a, 44b, 44c, and 44d may be pressed to select a corresponding function indicated by the respective soft key icon. For example, the soft key 44a may be pressed to display "LIMITS" information, while the soft key 44b may be pressed to display a "TREND" information. In certain embodiments, the soft keys 44 may be programmed to display operating information such as alarm limits, historic trends, setup menus, and alarm volume settings, among others. Moreover, a caretaker may actuate the soft keys 44 to display various operating menus, and then may use the arrow keys 38 to adjust operating parameters. Further, in certain embodiments, a caretaker may navigate through the user interface of the patient monitor 10 using the soft keys 44 and the fixed function keys (e.g., 32 and 38) to set user preferences that may be stored within the faceplate 12.

In addition to the selectable inputs 16, the faceplate 12 may include various indicators 48 (e.g., indicator lights and display screen graphics) that facilitate operation of the monitor 10 and observation of a patient's physiological metrics (e.g., pulse rate). Some of the indicators 48 are specifically provided to facilitate monitoring of a patient's physiological parameters. For example, the indicators 48 may include representations of the most recently measured values for $SpO_2$, pulse rate, and pulse amplitude. Other indicators 48 may be specifically provided to facilitate operation of the monitor 10. For example, the indicators 48 may include an A/C power indicator, a low battery indicator, an alarm silence indicator, a mode indicator, and so forth. The faceplate 12 also includes a speaker 50 for emitting audible indications (e.g., alarms). In certain embodiments, the speaker 50 and/or the display 18 may be included within the body 14 and the faceplate 12 may include a window, cover, or the like, that permits access to the speaker 50 and/or the display 18. However, in other embodiments, the speaker 50 and/or the display 18 may be included within the faceplate 12.

Multiple caretakers may be responsible for a patient's care, and accordingly, several different caretakers may operate the patient monitor 10. For example, nurses may rotate based on hospital shifts. Further, the patient monitor 10 may be employed in different environments, such as a patient's hospital room, a patient's home, or an operating room. Depending on the environment, various user interfaces may be desired. For example, in an operating room, it may be desirable to include larger buttons that facilitate operation with gloves. In another example, in a home environment, it may be desirable to disable certain adjustment features. In yet another example, a left handed user may prefer that the arrows 38 and the alarm silence button 32 be included on the left hand side of the display 18 to reduce blockage of the display 18 during actuation of the buttons 32 and 38. Further, certain caretakers may prefer different types of selectable inputs 16, such as knobs, wheels, or larger buttons, among others.

Accordingly, the faceplate 12 may be detachable from the body 14 to allow different faceplates to be mounted on the patient monitor 10. Specifically, the faceplate 12 may be coupled to the body 14 by an attachment mechanism 52 that may be actuated to remove and attach different faceplates 12. Each faceplate 12 may include different types of selectable inputs 16. For example, in certain embodiments, the size, shape, locations, and/or labels for the selectable inputs 16 may vary. Further, some or all of the selectable inputs 16 may include different types of inputs, such as knobs, buttons, slide bars, joysticks, and/or wheels, among others. Moreover, the labels, symbols, and/or types of indicators 48 may vary.

Figure 2:
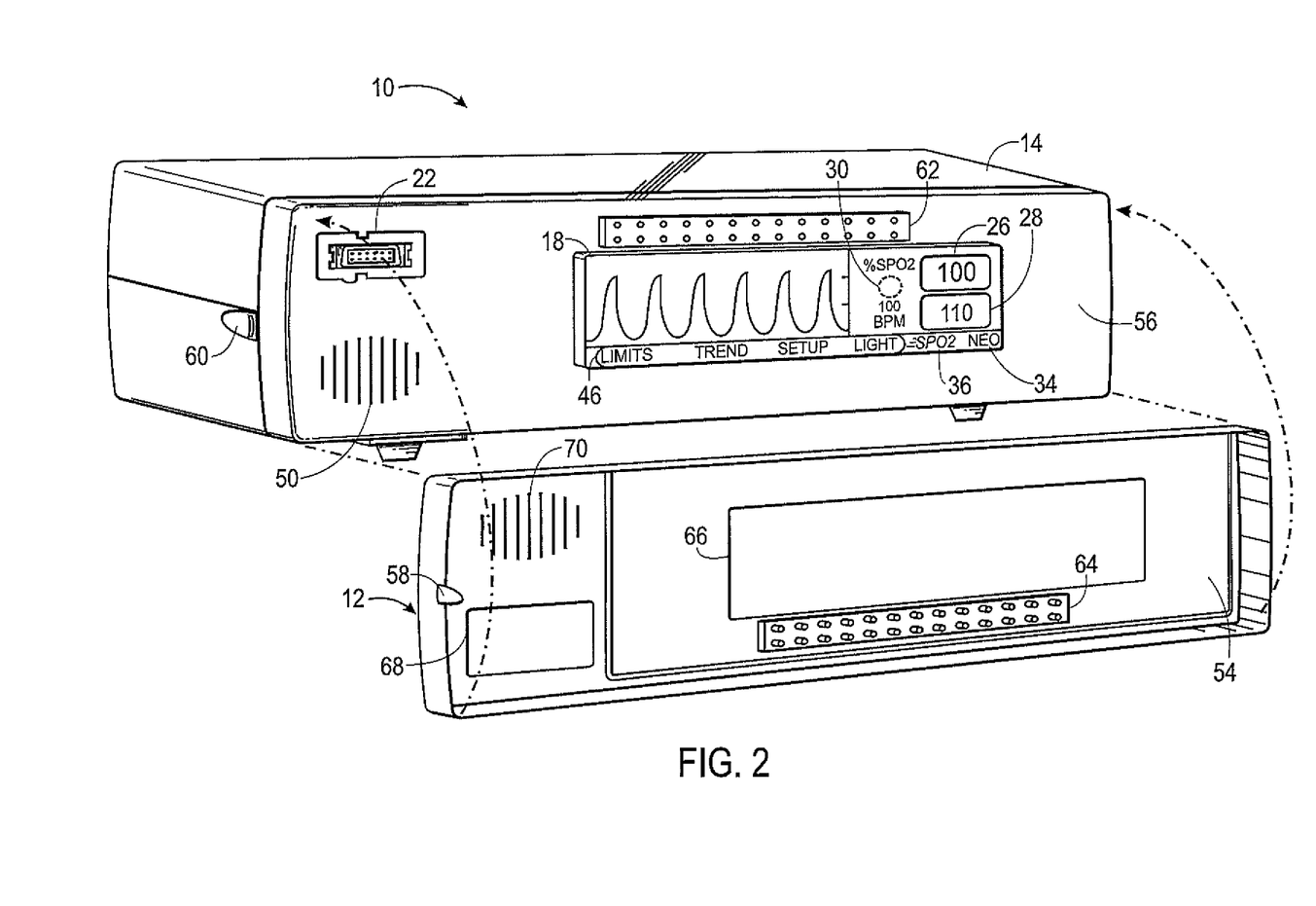
FIG. 2 is a perspective view of the patient monitor of FIG. 1 with the interchangeable faceplate removed.

FIG. 2 depicts the faceplate 12 removed from the device body 14 to reveal an interior surface 54 of the faceplate 12 that may be disposed against a front surface 56 of the device body 14. As shown in FIG. 2, the faceplate 12 may be physically attached to the body 14 by the use of connectors 58 and 60 that may mechanically couple together to form the attachment mechanism 52 shown in FIG. 1. Specifically, the connector 58 may include a clip designed to fit within a corresponding slot of the connector 60. Although not shown, additional pairs of the connectors 58 and 60 may be included on other sides of the device 14 and faceplate 12. Further, in other embodiments, other types of connectors 58 and 60, such as pins, brackets, or the like, may be employed.

In addition to being mechanically fastened to the device body 14, the faceplate 12 may be electrically coupled to the body 14 by electrical communication interfaces 62 and 64. Specifically, the device body 14 may include an electrical communication interface or receptacle 62 designed to mate with an electrical communication interface or plug 64 of the faceplate 12. In certain embodiments, the plug 64 may include electrical pin connections designed to fit within corresponding holes of the receptacle 62. However, in other embodiments, any suitable type of electrical communication interfaces 62 and 64 may be employed, such as, wire harnesses and plugs, or wireless connections, among others. When coupled to one another, the electrical communication interfaces 62 and 64 may enable electrical communications between the faceplate 12 and the body 14. For example, when an input is selected on the faceplate 12, a corresponding signal may be sent through the communication interfaces 62 and 64 to the device body 14.

The faceplate 12 also includes windows or openings 66, 68, and 70 that facilitate access to components included on the front surface 56 of the device body 14. Specifically, a window 66 may be designed to surround and allow access to the display 18. Another window 68 allows access to the medical device interface 22. Further, a vent 70 permits functionality of the speaker 50.

Figure 3:
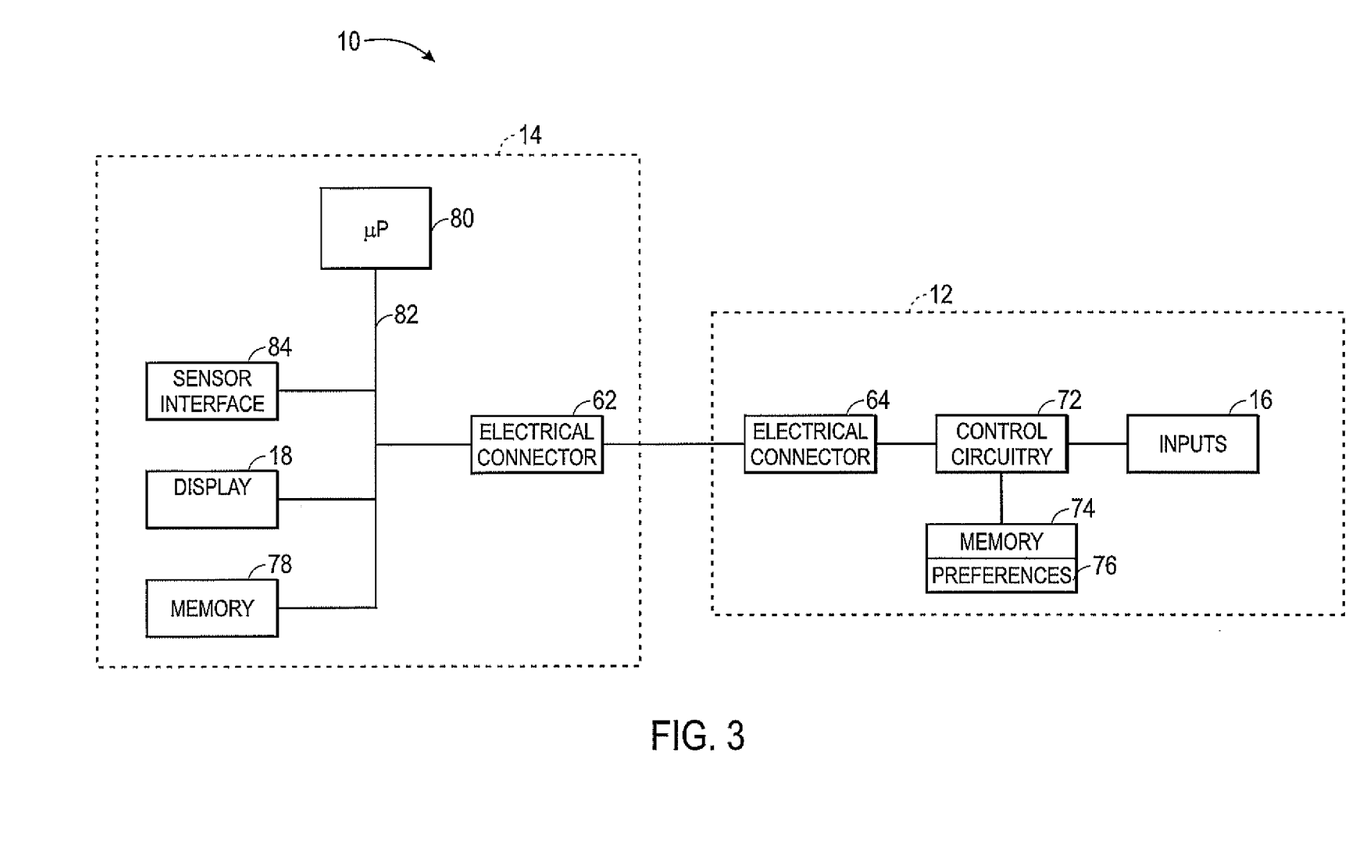
FIG. 3 is a block diagram of an embodiment of the patient monitor of FIG. 1.

FIG. 3 is a block diagram of the embodiment of the patient monitor 10 shown in FIGS. 1 and 2. The patient monitor 10 includes the faceplate 12 and the body 14 coupled to one another through the electrical communication interfaces 62 and 64. The faceplate 12 also includes control circuitry 72 that may route signals from the selectable inputs 16 to the electrical communication interface 64 for transmission to the device body 14. For example, the control circuitry 72 may include electrical circuits and components for transmitting signals between the selectable inputs 16 and the electrical communication interface 64. Moreover, in certain embodiments, the control circuitry 72 may include microprocessors and/or related chip sets, an interface board, and an analogue and digital converter, among others. Further, the electrical communication interface 64 may include one or more control interfaces for receiving input signals from the selectable inputs 16 via the electrical communication interface 62.

The faceplate 12 also may include a memory 74. The memory 74 may include volatile memory, such as random access memory (RAM) and/or non-volatile memory, such as read-only memory (ROM), and the like. In certain embodiments, the memory may store data representing user interface preferences 76. For example, the preferences 76 may include preferred display formats for the patient physiological data, such as display views (e.g., whether a pleth waveform or a blip bar is shown), default trend displays (e.g., whether the trend display defaults to a oxygen saturation display, a pulse rate display, a dual display, or a histogram), the display scale (e.g., the time range or amplitude range for the pleth waveform), and the display locations (e.g., where the physiological data is located on the display 18). The preferences 76 also may include preferred operating parameters, such the pulse beep volume, the alarm volume and/or duration, the alarm limits, and the response mode, among others. Further, the preferences 76 may include preferred user interface display formats, such as the preferred display language, icon size or symbol set, and the size of display areas and/or buttons (e.g., touch-sensitive button locations and/or sizes in embodiments employing a touch screen), among others.

According to certain embodiments, the preferences 76 also may specify the location of components of the user interface on the display 18. As noted above, each faceplate 12 may include different numbers, sizes, shapes, types, and/or locations of selectable inputs 16. The preferences 76 may specify the text and/or the location of labels on the display 18 that correspond to the selectable inputs 16. For example, the preferences 76 may identify the location and/or labels for the soft key menu 46 shown in FIG. 1. Further, the preferences 76 may ensure that the selectable inputs 16 align with the menu options shown on the display 18.

The preferences 76 may be entered by a user through the faceplate 12, for example, by navigating through menus using the selectable inputs 16. Upon entry, a user may save the preferences 76 to the memory 74. The preferences 76 may then be stored within the memory 74 and transmitted through the control circuitry 72 to the device body 14 upon attachment of the faceplate 12. For example, electrical communication interface 62 of the device body 14 may include a memory interface for reading the preference data from the memory 74 of the faceplate 12 via the electrical communication interface 64.

As shown, the preferences 76 are stored within the memory 74 of the faceplate 12. However, in other embodiments, the preferences 76 may be stored within a memory 78 of the device body 14. For example, in certain embodiments, the faceplate 12 may transmit a unique identifier, such as a serial number stored within the memory 74, to the device body 14 upon attachment of the faceplate 12. Upon receiving the unique identifier, the device body 14 may retrieve preferences associated with the unique identifier from the memory 78 of the device body 14. The memory 78 also may store various screens, templates, layers, and the like that may shown on the display 18 as part of the user interface for the patient monitor 10.

In certain embodiments, the device body 14 may apply the preferences 76 in response to detecting connection of the faceplate 12. The device body 14 generally includes a microprocessor 80 connected to an internal bus 82. In certain embodiments, the microprocessor 80 may detect connection of the faceplate 12 through the electrical communication interface 62. The microprocessor 80 may then operate the patient monitor 10 based on the preferences 76. Moreover, in certain embodiments, the microprocessor 80 may select certain screens of the user interface based on the preferences 76 received from the faceplate 12. For example, the microprocessor 80 may select screens with appropriate labels, icons, and the like that correspond to the types, positions, and numbers of the input devices 16 included in the faceplate 12.

In addition to the memory 78, the display 18, and the communication interface 62, a sensor interface 84 also may be connected to the bus 82. The sensor interface 84 may allow the device 14 to communicate with and receive physiological data from the sensor 20 (FIG. 1). In certain embodiments, the sensor interface 84 may include components, such as a decoder for decoding signals from the sensor, algorithms or lookup tables for identifying physiological parameters, drive circuits, and signal-processing equipment, such as filters, analog to digital converters, amplifiers, queued serial modules, and time processing units, among others.

In general, the sensor interface 84 may be designed to receive input from the sensor 20 and transmit signals to the microprocessor 80 in a form that the microprocessor may use to calculate and/or to determine physiological parameters, for example, based on algorithms or look-up tables stored in the memory 78. In certain embodiments, the microprocessor 80 may use the information from the sensor interface 84 to determine physiological parameters, such as $SpO_2$, pulse rate, respiratory effect, and so forth. The physiological parameters may then be displayed on the display 18. For example, as shown in FIG. 1, the physiological parameters, such as the pleth waveform 24, the pulse rate 28, and the oxygen saturation 26, may be shown on the display 18.

Figure 4:
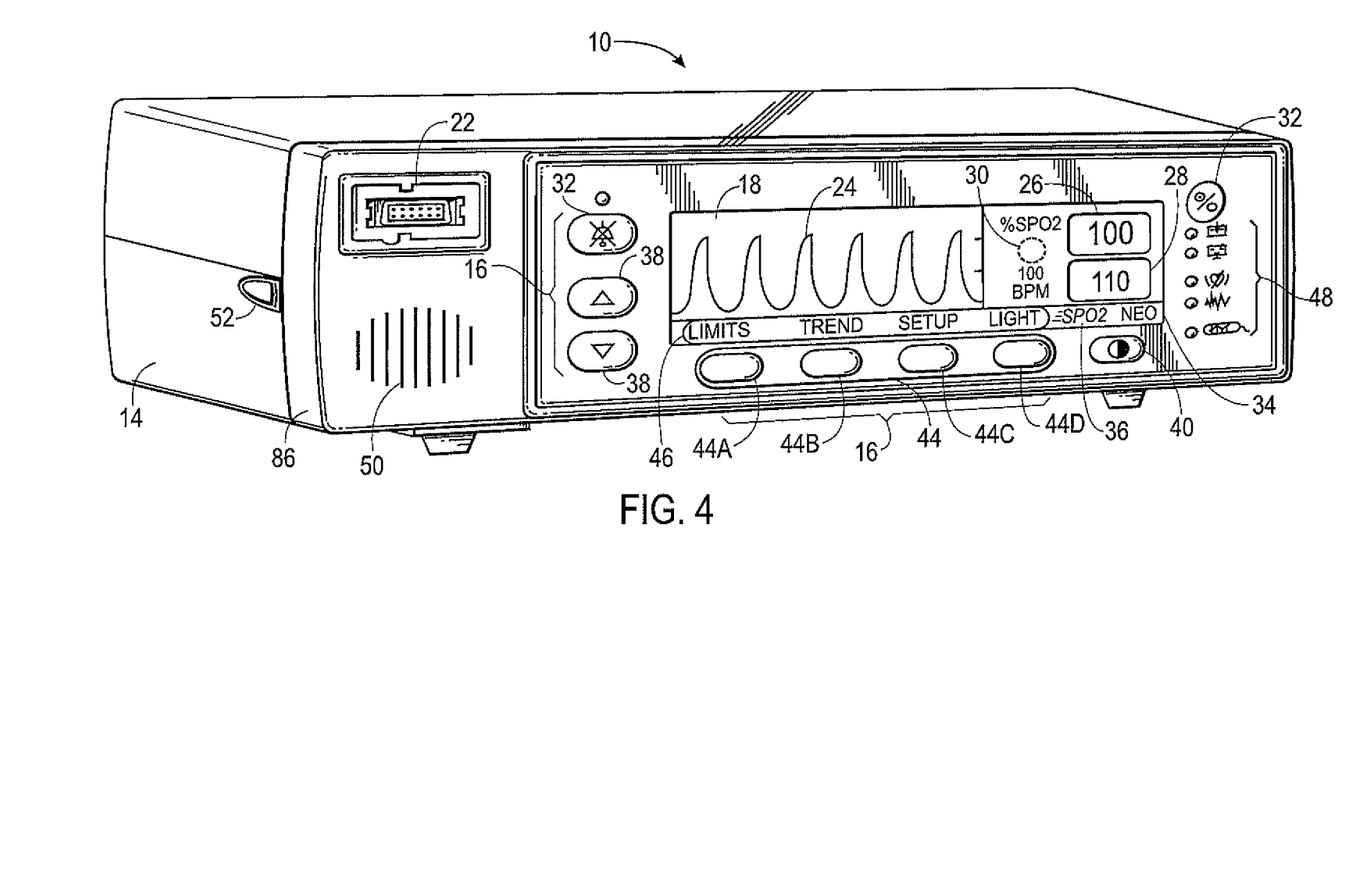
FIG. 4 is a perspective view of another embodiment of an interchangeable faceplate attached to a patient monitor.

FIG. 4 depicts another embodiment of a faceplate 86 that may be coupled to a device body 14. The faceplate 86 may include the electrical communication interface 64, the control circuitry 72, and the memory 74 as shown in FIG. 3. However, as may generally be seen by comparing FIGS. 1 and 4, the configuration of the selectable inputs 16 included in the faceplate 86 of FIG. 4 may be different from the configuration of the selectable inputs 16 included in the faceplate 12 of FIG. 1. Specifically, as shown in FIG. 1, the alarm silence button 32 and the arrows 38 are located on the right-hand side of the monitor 10 while the indicators 48 are located on the left-hand side of the monitor 10. The faceplate 86, as shown in FIG. 4, reverses the positions of these selectable inputs 16 and indicators 48. Specifically, as shown in FIG. 4, the buttons 32 and 38 are located on the left-hand side of the monitor 10 while the indicators 48 are located on the right-hand side of the monitor 10. In certain embodiments, the faceplate 86 may be designed to facilitate use by a left-handed user by allowing a user to select the buttons 32 and 38 without reaching across the display 18.

In other embodiments, other types of faceplates may be employed to allow further customization of the patient monitor 10. For example, faceplates may be used to change the locations of the selectable inputs 16, the sizes of the selectable inputs 16, the types of the selectable inputs 16, and/or the symbols shown on the selectable inputs 16, as well as the locations, sizes, end symbols for the indicators 48. Moreover, in certain embodiments, individual caretakers may each possess their own faceplate, allowing each caretaker to select a preferred configuration of selectable inputs 16 and/or to store their selected preferences 76 in their own faceplate.

Figure 5:
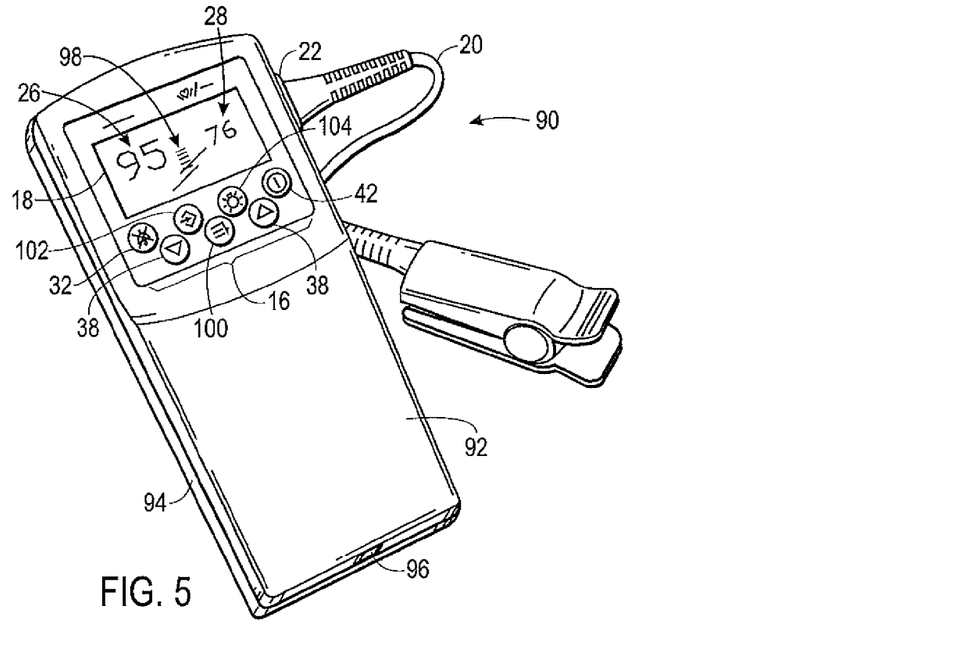
FIG. 5 is a perspective view of an embodiment of a handheld patient monitor with an interchangeable faceplate.

FIG. 5 depicts another embodiment of a patient monitor 90, in this case a handheld patient monitor 90. The patient monitor includes a faceplate 92 coupled to a device body 94 by an attachment mechanism, such as a clip 96. The clip 96 may allow the faceplate 92 to be removed and attached to the device body 94. Similar to the faceplate 12, the faceplate 92 may include the electrical communication interface 64, the control circuitry 72, and the memory 74. Further, the faceplate 92 may be electrically coupled to the device body 94 by connecting the electrical communication interface 64 of the faceplate 92 to a complementary electrical communication interface 62 of the device body 94.

The faceplate 92 shows the oxygen saturation 26, the pulse rates 28, and a blip bar 98 on the display 18. The blip bar 98 may generally display a pulse amplitude of the pleth waveform. The faceplate 92 also may include selectable inputs 16, such as a menu button 100 that may be used to display setup menus, alarm limit menus, trend menus, and the like, on the display 18. The selectable inputs 16 also may include the alarm silence button 32, the arrow keys 38, the power button 42, a data button 102 that may be used to print or save values shown on the display 18, and a backlight button 104 that may be selected to adjust or light up the display 18.

Figure 6:
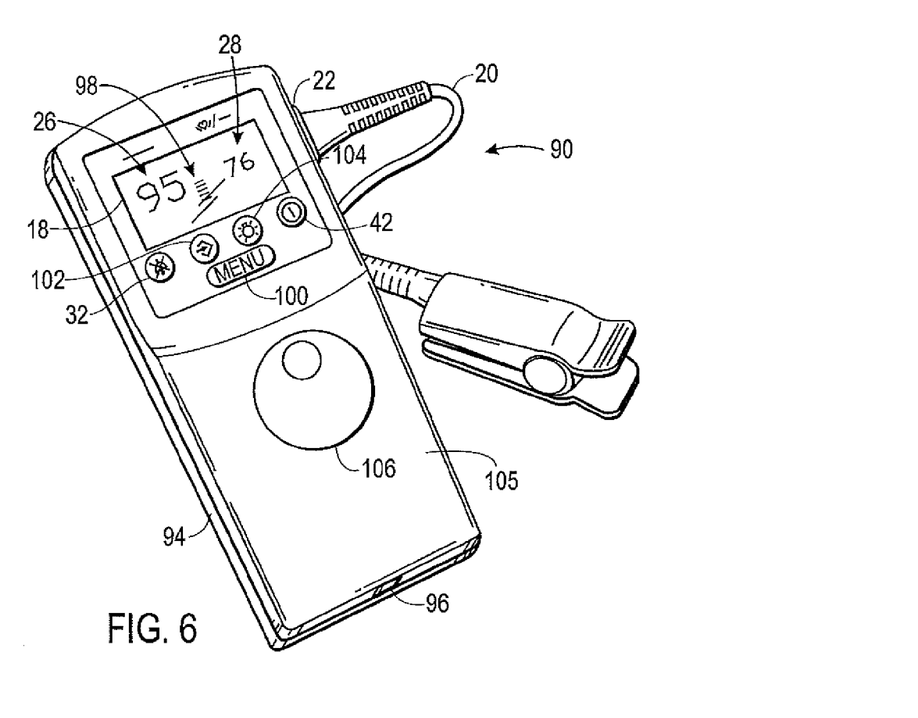
FIG. 6 is a perspective view of another embodiment of an interchangeable faceplate attached to a handheld patient monitor.

In order to customize the interface of the patient monitor 90, the faceplate 92 may be interchanged with other faceplates, such as a faceplate 105 shown in FIG. 6. The faceplate 105 includes the alarm silence button 32, the data button 102, the backlight button 104, and the power button 42. However, instead of the arrow buttons 38, a knob 106 has been included on the faceplate 105. Specifically, the knob 106 includes a circular structure that may be rotated to increase or decrease values shown on the display 18. The menu button 100 also has been increased in size to accommodate a user who prefers a larger size button.

Figure 7:
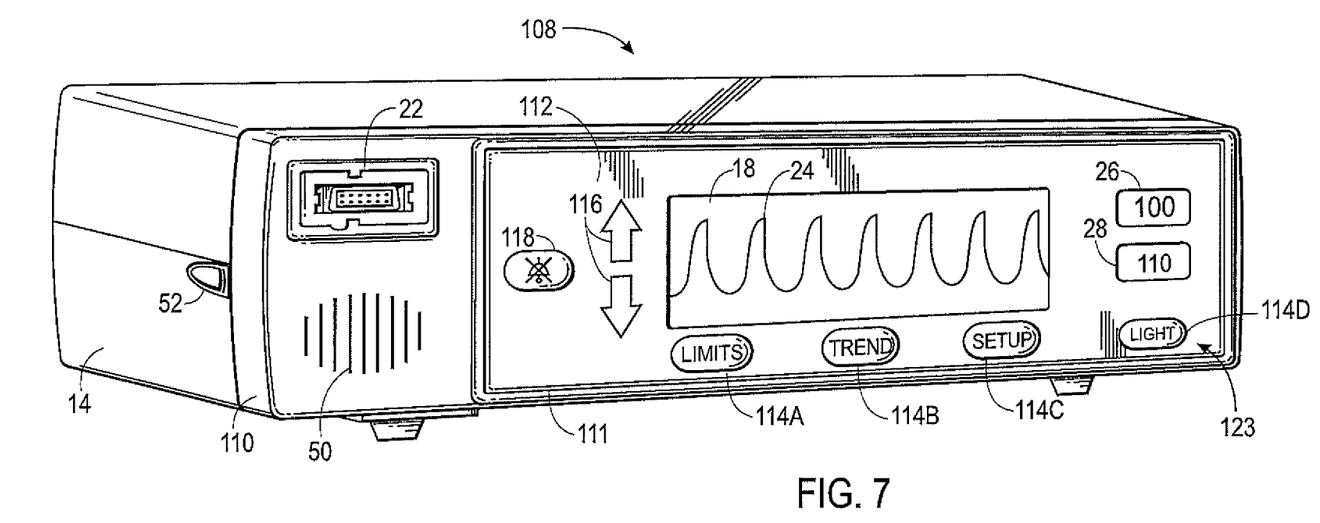
FIG. 7 is a perspective view of an embodiment an interchangeable faceplate attached to a patient monitor employing a touch screen.

The interchangeable faceplates described herein also may be employed in patient monitors that include a touch screen. For example, as shown in FIG. 7, a patient monitor 108 includes a faceplate 110 with a window 111 designed to allow access to a touch screen 112. The touch screen 112 may allow a caregiver to select touch sensitive inputs 114, 116, and 118, shown on the touch screen 112. Specifically, the touch sensitive inputs may be included on a screen 123 of a graphical user interface of the patient monitor 108. The screen 123 may show the pleth waveform 24, the oxygen saturation 26, and the pulse rate 28 in addition to the inputs 114, 116, and 118.

Instead of, or in addition to, using the selectable inputs 16 shown in FIG. 1, a user may control operation of the patient monitor 108 by selecting the touch sensitive inputs 114, 116, and 118. For example, a user may select the soft key icons 114 to access corresponding menus. A user may then navigate through the menus by selecting the arrow icons 116. In another example, a user may silence an alarm by selecting the alarm silence icon 118.

The faceplate 112 also includes the memory 74 (FIG. 3) that may store preferences 76 (FIG. 3) for the caregiver. For example, the preferences 76 may specify the types, sizes, locations, and symbols for the touch sensitive inputs 114, 116, and 118. In another example, the preferences 76 may specify alarm limits, display preferences, and trend views, among other preferences. In other embodiments, the preferences 76 may be stored within the memory 78 (FIG. 3) of the device body 14 and accessed using a unique identifier of the faceplate 110.

Figure 8:
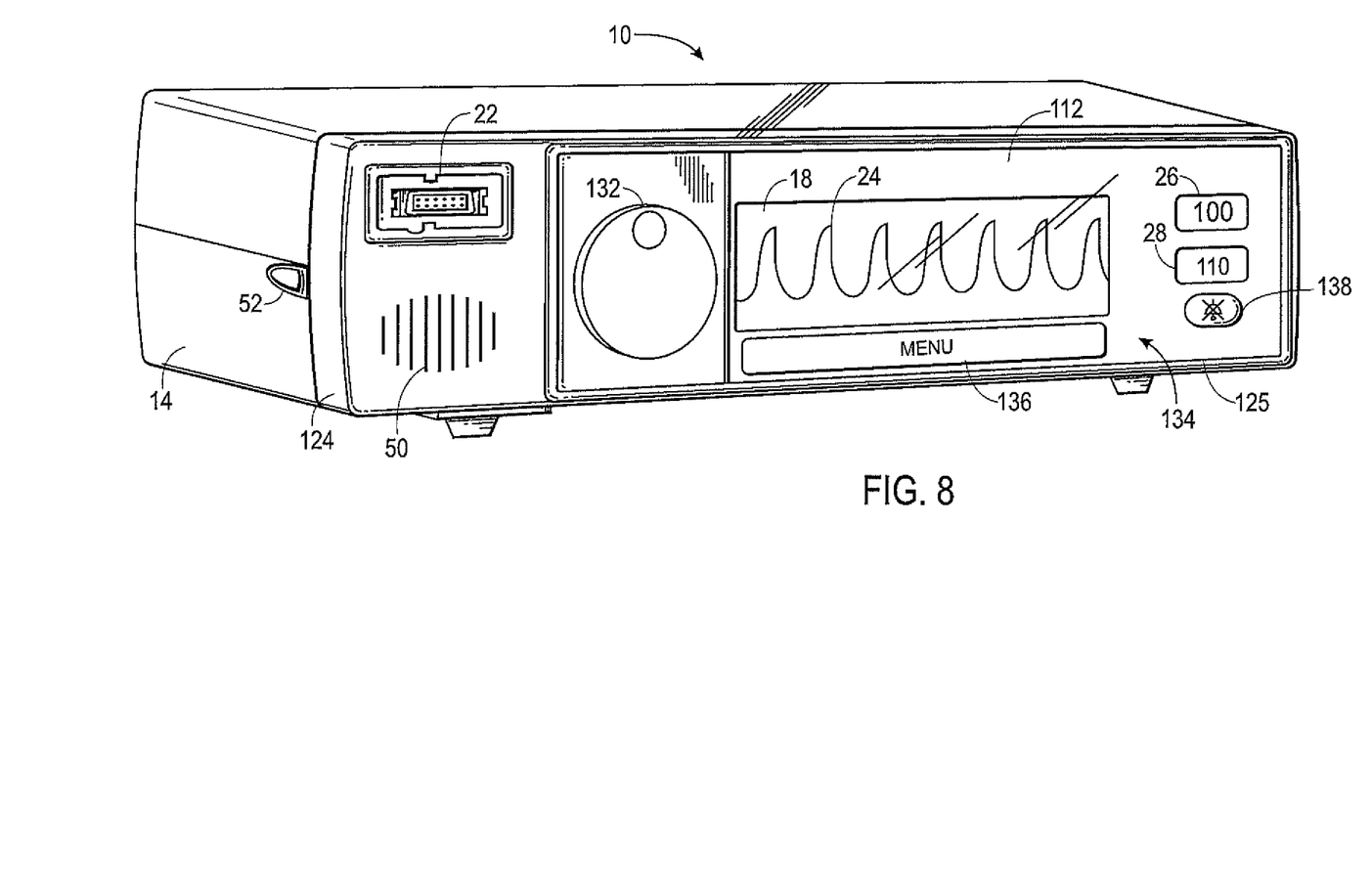
FIG. 8 is a perspective view of another embodiment of an interchangeable faceplate attached to a patient monitor employing a touch screen.

The faceplates described herein also may allow users to customize selectable inputs 16 for use with patient monitors employing touch screens. For example, as shown in FIG. 8, another embodiment of a faceplate 124 includes a window 125 designed to allow access to a portion of the touch screen 112. The remaining portion of the touch screen 112, previously occupied by the touch sensitive inputs 116 and 118, shown in FIG. 7, may be covered by a physical knob 132. The knob 132 may be designed for users that prefer physical manipulation of alarm limits to manipulation of touch screen arrows 116 (FIG. 7). To accommodate the physical knob 132, the display area of the touch screen 112 may be reduced in size to show a screen 134 that only occupies the visible area provided by the window 125. The screen 134 includes a touch sensitive menu icon 136 that may be actuated by a user to show various operating menus and/or setup menus. The screen 134 also includes an alarm silence touch sensitive icon 138 that may be actuated to silence alarms.

As may be appreciated, the faceplates describe above with respect to FIGS. 1-8 may be employed with displays with or without touch screens. Furthermore, any combination of the faceplate features described herein may be employed. Moreover, the relative sizes, shapes, numbers, and geometries of the faceplate features, such as the indicator lights, the selectable inputs 16, the touch sensitive inputs, the displays, and the windows, may vary.

What is claimed is:

1. A patient monitor, comprising: a device body comprising one or more medical device interfaces suitable for connection to a sensor or to a therapy device; a display configured to display: patient physiological data based on input received from the sensor or the therapy device; and one or more user selectable interface options; an electrical communication interface disposed in the device body; and a faceplate configured to be coupled to the device body through the electrical communication interface and comprising a memory configured to receive user interface data from the device body and store the one or more user selectable interface options, wherein the faceplate is configured to transfer the one or more user selectable interface options stored in the memory to the device body through the electrical communication interface when the faceplate is connected to the device body.

2. The patient monitor of claim 1, wherein the device body comprises a physical attachment mechanism configured to secure the faceplate to the device body and detaching the interchangeable faceplate from the device body.

3. The patient monitor of claim 1, wherein the patient physiological data comprises a plethysmographic waveform, an oxygen saturation, a pulse rate, or combinations thereof.

4. The patient monitor of claim 1, wherein the one or more user selectable interface options comprise alarm limits, an alarm volume, or display formats for the patient physiological data, or combinations thereof.

5. The patient monitor of claim 1, wherein the electrical communication interface comprises one or more control interfaces for receiving input signals from selectable inputs disposed on the faceplate.

6. The patient monitor of claim 1, wherein the electrical communication interface comprises a memory interface for reading data from a memory disposed in the faceplate.

7. The patient monitor of claim 1, wherein the selectable inputs comprise buttons, or knobs, or combinations thereof.

8. A patient monitoring system, comprising:
a device body comprising a medical device interface for receiving input related to patient physiological data;
a display configured to display the patient physiological data and displaying a user interface for controlling operation of the patient monitoring system; and
one or more faceplates each configured to be coupled to the device body and each comprising a memory for receiving user interface data from the device body and storing the user interface data.

9. The patient monitoring system of claim 8, wherein the display comprises a touch screen, and wherein the display varies the location of user selectable inputs on the touch screen based on the user interface data received from the one or more faceplates.

10. The patient monitoring system of claim 8, wherein the one or more faceplates each comprise a window that surrounds the display upon attachment to the device body.

11. The patient monitoring system of claim 8, wherein the user interface data comprises a unique identifier for at least one of the interchangeable faceplates, and wherein the device body comprises a memory configured to store user interface preferences associated with the unique identifier.

12. The patient monitoring system of claim 8, wherein the user interface data comprises user interface preferences specifying alarm limits, display scales for the patient physiological data, or display locations for the patient physiological data, or combinations thereof.

13. The patient monitoring system of claim 8, comprising two or more interchangeable faceplates each comprising selectable inputs for manipulating the user interface, and wherein the selectable inputs differ in at least one of size, type, or location between the two or more interchangeable faceplates.

14. The patient monitoring system of claim 8, comprising a processor configured to vary at least portions of the user interface based on which faceplate of the one or more faceplates is attached to the device body.

15. The patient monitoring system of claim 8, wherein the device body comprises a first mechanical attachment mechanism and the one or more faceplates each comprise a second mechanical attachment mechanism configured to mate with the first mechanical attachment mechanism to secure the one or more faceplates to the device body.

16. The patient monitoring system of claim 8, wherein the device body comprises a first electrical communication interface and the one or more faceplates each comprise a second electrical communication interface configured to connect with the first electrical port to allow electrical communications between the one or more faceplates and the device body.

17. A removable faceplate for a patient monitor, comprising:
user selectable input structures suitable for controlling operation of a patient monitor;
an electrical communication interface suitable for allowing at least electrical communications between the user selectable input structures and a complementary electrical communication interface of the patient monitor, wherein the electrical communication interface is configured to receive user interface data related to an operation of the patient monitor from the monitor; and
a memory configured to store the user interface data, wherein the user interface data is transmitted through the electrical communication interface when the faceplate is attached to the patient monitor.

18. The removable faceplate of claim 17, wherein the removable faceplate is configured to mount to a front surface of the patient monitor to allow access to a display of the patient monitor.

19. The removable faceplate of claim 17, comprising a window configured to surround a display of the patient monitor and wherein the user selectable input structures are configured to align with menu options displayed on the display of the patient monitor.

20. The removable faceplate of claim 17, wherein the user interface data comprises alarm limits, an alarm volume, or display formats for the patient physiological data, or combinations thereof.

* * * * *